(12) United States Patent
Lau (10) Patent No.: US 10,776,737 B2
(45) Date of Patent: Sep. 15, 2020

(54) SYSTEM AND METHOD FOR GENERATING OPERATIONAL METRICS DATA FOR A MEDICAL CARE FACILITY

(71) Applicant: Karl Storz Endoscopy-America, Inc., El Segundo, CA (US)

(72) Inventor: Stephen Lau, Houston, TX (US)

(73) Assignee: Karl Storz Endoscopy-America, Inc., El Segundo, CA (US)

( * ) Notice: Subject to any disclaimer, the term of this patent is extended or adjusted under 35 U.S.C. 154(b) by 670 days.

(21) Appl. No.: 15/227,494

(22) Filed: Aug. 3, 2016

(65) Prior Publication Data
US 2018/0039923 A1   Feb. 8, 2018

(51) Int. Cl.
G06Q 10/06     (2012.01)
G06Q 50/22     (2018.01)
G16H 40/20     (2018.01)

(52) U.S. Cl.
CPC ... G06Q 10/0637 (2013.01); G06Q 10/06393 (2013.01); *G06Q 50/22* (2013.01); *G16H 40/20* (2018.01)

(58) Field of Classification Search
CPC ......... G06Q 10/0637; G06Q 10/06393; G06Q 50/22; G16H 40/20
See application file for complete search history.

(56) References Cited

U.S. PATENT DOCUMENTS

| 5,374,813 | A  | * | 12/1994 | Shipp ................... | G06Q 10/08 235/375 |
| 8,740,082 | B2 | * | 6/2014  | Wilz, Sr. ............. | G06K 7/10584 235/462.01 |
| 8,781,920 | B2 |   | 7/2014  | Kreiner et al. | |
| 9,847,044 | B1 | * | 12/2017 | Foster .................... | G09B 23/28 |
| 2008/0255880 | A1 | * | 10/2008 | Beller ................... | G06Q 10/00 705/3 |
| 2011/0001605 | A1 | * | 1/2011  | Kiani ................... | G06F 19/3418 340/5.6 |
| 2011/0307284 | A1 | * | 12/2011 | Thompson ....... | G06Q 10/06311 705/7.13 |

(Continued)

OTHER PUBLICATIONS

"Workflow and activity modeling for monitoring surgical procedures", N Padoy—2010—tel.archives-ouvertes.fr (Year: 2010).*

(Continued)

*Primary Examiner* — Jonathan G Sterrett
(74) *Attorney, Agent, or Firm* — Whitmyer IP Group LLC (57) ABSTRACT

A system for generating operational metrics data for a medical care facility includes a first camera and an operational metrics device. The first camera generates digital images of a first detection area. The operational metrics device includes an optical code detector, a medical object detector, and an operational metrics generator. The optical code detector generates optical code detection data indicative of the presence or absence of optical codes within each of the digital images. Each of the optical codes is disposed on a respective medical object. The medical object detector generates medical object detection data indicative the presence or absence of each medical object within the first detection area. For each medical object, the operational metrics generator generates operational metrics data based at least partially on a determined amount of time that each medical object was present within the first detection area.

31 Claims, 6 Drawing Sheets

(56) References Cited

U.S. PATENT DOCUMENTS

| | | | | |
|---|---|---|---|---|
| 2012/0154582 | A1* | 6/2012 | Johnson | G06F 19/321 |
| | | | | 348/143 |
| 2012/0191476 | A1* | 7/2012 | Reid | G06Q 50/24 |
| | | | | 705/3 |
| 2012/0245948 | A1* | 9/2012 | Nolte | G06Q 10/10 |
| | | | | 705/2 |
| 2014/0081659 | A1* | 3/2014 | Nawana | G16H 50/20 |
| | | | | 705/3 |
| 2014/0249850 | A1* | 9/2014 | Woodson | G06F 19/3481 |
| | | | | 705/3 |
| 2015/0127362 | A1 | 5/2015 | DeBusk et al. | |
| 2016/0267806 | A1* | 9/2016 | Hsu | G09B 19/24 |
| 2019/0006047 | A1* | 1/2019 | Gorek | A61B 17/00 |

OTHER PUBLICATIONS

New technologies for information retrieval to achieve situational awareness and higher patient safety in the surgical operating room: the MRI institutional . . . M Kranzfelder, A Schneider, S Gillen, H Feussner—Surgical endoscopy, 2011—Springer (Year: 2011).*

A smart trocar for automatic tool recognition in laparoscopic surgery G Toti, M Garbey, V Sherman, BL Bass . . . -Surgical . . . , 2015-journals.sagepub.com (Year: 2015).*

AXIS P33 Network Camera Series, retrieved from the web at: https://www.axis.com/en-us/products/axis-p33-series, on Sep. 25, 2019 (Year: 2019).*

Trends in Surgery-Suite Design, Part One, Health Care Design Mag, Luoma, Harrison, May 31, 2007 (Year: 2007).*

What is the minimum size for a QR code, Flanagan, Dec. 1, 2013, retrieved from https://www.qrcode.es/en/what-is-the-minimum-size-for-a-qr-code/ (Year: 2013).*

What Size Should A Printed QR Code Be? Posted: Jan. 18, 2011, retrieved from https://blog.qrstuff.com/2011/01/18/what-size-should-a-qr-code-be (Year: 2011).*

AXIS P33 Series User's Manual Rev. 1.1 Copyright © Axis Communications AB, 2009 Jul. 2009 Part No. 34463 (Year: 2009).* https://en.wikipedia.org/wiki/QR_code, retrieved from the web on Sep. 25, 2019. (Year: 2019).*

Low resolution QR-code recognition by applying super-resolution using the property of QR-codes Y Kato, D Deguchi, T Takahashi, I Ide . . . - . . . on Document Analysis . . . , 2011-ieeexplore.ieee.org (Year: 2011).*

QR Code Minimum Size: Calculate ideal size for your use case, Gautam Garg | Feb. 20, 2015, retrieved from https://scanova.io/blog/blog/2015/02/20/qr-code-minimum-size/ (Year: 2015).*

Trico Welding Supplies, Acetylene Cylinder Sizing chart, © 2011. (Year: 2011).*

AXIS P33 Network Camera Seriess, "Fixed domes for any environment with remote focus and zoom", http://www.axis.com/us/en/products/axis-p33-series, 2016.

Qtechnology A/S, "Need a tailored solution?", http://qtec.com/index.html%3Fp=310.html, Copyright 2016.

* cited by examiner

SYSTEM AND METHOD FOR GENERATING OPERATIONAL METRICS DATA FOR A MEDICAL CARE FACILITY

TECHNICAL FIELD

Aspects of the present invention generally relate to a system and method for generating operational metrics data, and more particularly relates to a system and method for generating operational metrics data for a medical care facility.

BACKGROUND

Medical care facilities (e.g., hospitals) are under constant pressure to increase operational efficiencies, and to lower operational costs. Attempts to achieve these goals are often hindered by the fact that it can be difficult to obtain accurate information regarding, among other things: (i) the types of medical procedures (e.g., checkups, surgeries, etc.) that are being performed in a medical care facility, or in particular area thereof (e.g., the operating room, the emergency room, etc.); (ii) an amount of time spent performing each medical procedure; (iii) identities of the medical personnel (e.g., doctors, nurses, medical assistants, etc.) involved in a medical procedure; (iv) amounts of time patients spend in the medical care facility, or in a particular area thereof, before, during, and/or after a medical procedure; and (v) the types of medical objects (e.g., medical tools, medical equipment, pieces of medical clothing worn by medical professionals, etc.) that are used or present during a medical procedure.

Various systems and methods have been developed to aid in monitoring medical personnel and/or medical objects within a medical care facility, or a particular area thereof. However, these systems and methods can be expensive, can require burdensome user involvement, and/or can be limited in their ability to provide the above-described information.

For example, it is known to provide a patient with a bracelet that includes a patient identification bar code. At least one room of the medical care facility can be outfitted with a laser scanner that can be used to scan the patient identification bar code each time the patient enters or exits the room. Such systems can provide useful information regarding the amount of time a patient spends within the room outfitted with the laser scanner; however, such systems can be problematic in that they require substantial user involvement. That is, such systems require that medical personnel scan the patient identification bar code each time the patient enters or exits the room. During busy periods or medical emergencies, medical personnel may purposefully skip the step of scanning the patient identification bar code in order to save time, thereby preventing the system from achieving its intended purpose. Such systems can also be problematic in that the bracelet typically needs to be brought into contact with the laser scanner. As a result, the laser scanner can collect germs from each bracelet, or from the patient on which each bracelet is disposed, and can thus cause or contribute to the spread of germs between and among patients within the medical care facility.

As another example, it is known to provide a medical object that includes a radio-frequency identification (RFID) transmitter. An RFID detector can be used to detect the presence or absence of the RFID transmitter within a particular area of a medical care facility. The detection of the RFID transmitter can be used to generate useful information indicative of the presence or absence of the medical object within the particular area of the medical care facility. However, it can be difficult or impossible to retrofit existing medical objects with an RFID transmitter, and it can be prohibitively expensive to replace all existing medical objects with corresponding medical objects that include RFID transmitters. Also, RFID detectors can detect the presence or absence of RFID transmitters within a particular area, but they are limited in their ability to detect and/or monitor movement of RFID transmitters within the particular area.

Aspects of the present invention are directed to these and other problems.

SUMMARY

According to an aspect of the present invention, a system for generating operational metrics data for a medical care facility is provided. The system includes a first camera and an operational metrics device. The first camera is configured to generate a first plurality of digital images of a first detection area during a first detection period. Each of the first plurality of digital images is representative of the first detection area at one of a first plurality of discrete imaging times during the first detection period. The operational metrics device includes optical code detector, a medical object detector, and an operational metrics generator. The optical code detector is configured to generate optical code detection data indicative of at least a presence or absence of one or more optical codes within each of the first plurality of digital images. Each of the one or more optical codes is disposed on a respective medical object. The medical object detector is configured to receive the optical code detection data and generate medical object detection data therefrom. The medical object detection data is indicative of at least a presence or absence of each respective medical object within the first detection area at each of the first plurality of discrete imaging times during the first detection period. The operational metrics generator is configured to receive the medical object detection data from the medical object detector, and analyze the medical object detection data to determine, for each respective medical object, at least an amount of time that each respective medical object was present within the first detection area during the first detection period. The operational metrics generator is further configured to generate operational metrics data based at least partially on the determined amount of time that each respective medical object was present within the first detection area during the first detection period.

According to another aspect of the present invention, a method for generating operational metrics data for a medical care facility is provided. The method includes the steps of: (i) generating a first plurality of digital images of at least a first detection area within a medical care facility during a first detection period, each of the first plurality of digital images representative of the first detection area at one of a first plurality of discrete imaging times during the first detection period; (ii) generating optical code detection data indicative of at least a presence or absence of one or more optical codes within each of the first plurality of digital images, each of the one or more optical codes disposed on a respective medical object and providing a machine-readable representation of data regarding the respective medical object; (iii) using the optical code detection data to generate medical object detection data indicative of at least a presence or absence of each respective medical object within the first detection area at each of the first plurality of discrete imaging times during the first detection period; (iv) using the medical object detection data determine at least an amount of time that each respective medical object was present within the first detection area during the first detection period; and (v) generating operational metrics data based at least partially on the determined amount of time that each respective medical object was present within the first detection area during the first detection period.

In addition to, or as an alternative to, one or more of the features described above, further aspects of the present invention can include one or more of the following features, individually or in combination:

each of the one or more optical codes provides a machine-readable representation of data regarding the respective medical object on which the optical code is disposed;

a second camera is configured to generate a second plurality of digital images of a second detection area during a second detection period, each of the second plurality of digital images representative of the second detection area at one of a second plurality of discrete imaging times during the second detection period;

the optical code detection data generated by the optical code detector is indicative of the presence or absence of the one or more optical codes within each of the first plurality of digital images, and the presence or absence of the one or more optical codes within each of the second plurality of digital images, the medical object detection data is indicative of at least the presence or absence of each respective medical object within the first detection area at each of the first plurality of discrete imaging times, and the presence or absence of each respective medical object within the second detection area at each of the second plurality of discrete imaging times, the operational metrics generator is configured to determine, for each respective medical object, at least an amount of time that each respective medical object was present within the first detection area during the first detection period, and an amount of time that each respective medical object was present within the second detection area during the second detection period, and the operational metrics data is based at least partially on the determined amount of time that each respective medical object was present within the first detection area during the first detection period, and the determined amount of time that each respective medical object was present within the second detection area during the second detection period;

the first detection area is at least substantially the same as the second detection area;

the first detection area and the second detection area only partially overlap one another;

the first detection area and the second detection area do not overlap one another at all;

the first detection area and the second detection area are in a same room of a medical care facility;

the first detection area is in a first room, and the second detection area is in a second room remotely located relative to the first room;

the first room is in a first medical care facility, and the second room is in a second medical care facility remotely located relative to the first medical care facility;

the first detection area covers at least substantially an entirety of a room within a medical care facility;

the respective medical object is at least one of medical tool, a piece of medical equipment, and piece of medical clothing configured to be worn by a medical professional;

each of the one or more optical codes is a one-dimensional bar code;

each of the one or more optical codes is a two-dimensional bar code;

each of the one or more optical codes is a QR code;

at least one of the one or more optical codes reflects light at least substantially within a wavelength range that is easily perceived by a naked human eye;

at least one of the one or more optical codes reflects light at least substantially within a wavelength range that is not easily perceived, or is imperceptible, to a naked human eye;

the first camera includes a first sensor configured to capture and detect light from the first detection area and a second sensor configured to capture and detect light from the first detection area, the first sensor is an RGB sensor or a monochromatic sensor, and the second sensor is at least one of a monochromatic sensor, a near infrared sensor, a shortwave infrared sensor an infrared sensor, and a hyperspectral sensor;

all of the one or more optical codes reflect light at least substantially within a wavelength range that is not easily perceived, or is imperceptible, to a naked human eye, the first camera includes a light sensor configured to detect light at least substantially within a wavelength range that is not easily perceived, or is imperceptible, to a naked human eye, and the system does not include any light sensor configured to detect light at least substantially within a wavelength range that is easily perceived by a naked human eye;

the optical code detection data is further indicative of respective locations of the one or more optical codes within each of the first plurality of digital images, the medical object detection data is further indicative of respective locations of each respective medical object present within the first detection area at each of the first plurality of discrete imaging times, and the operational metrics generator is further configured to determine, and generate the operational metrics data at least partially based on, whether each respective medical object was moved during the first detection period;

the operational metrics generator is further configured to determine, and generate the operational metrics data at least partially on based on, a number of times that each respective medical object entered and/or exited the first detection area during the first detection period;

a user portal configured to permit a user to access, manipulate, and/or retrieve the operational metrics data generated by the operational metrics generator;

the first camera is positioned in a room of a medical care facility, and the user portal is remotely located relative to the room;

the first camera and the operational metrics device are discrete components that are remotely located relative to one another;

the first camera is positioned in a room of a medical care facility, and the operational metrics device is remotely located relative to the room;

at least one of the optical code detector, the medical object detector, and the operational metrics generator is included within the first camera;

at least one of the optical code detector, the medical object detector, and the operational metrics generator is remotely located relative to the first camera;

the operational metrics device receives the first plurality of digital images from the first camera via one or more wired and/or wireless connections, and the operational metrics device transmits the optical code detection data, the medical object detection data, and the operational metrics data via one or more wired and/or wireless connections; and one or more components are connected via a network connection, the network connection being at least one of an Internet connection, a personal area network connection, a local area network connection, and a wide area network connection.

These and other aspects of the present invention will become apparent in light of the drawings and detailed description provided below.

DETAILED DESCRIPTION

The present disclosure describes exemplary embodiments of a system 10 and related method for generating operational metrics data for a medical care facility.

Figure 1:
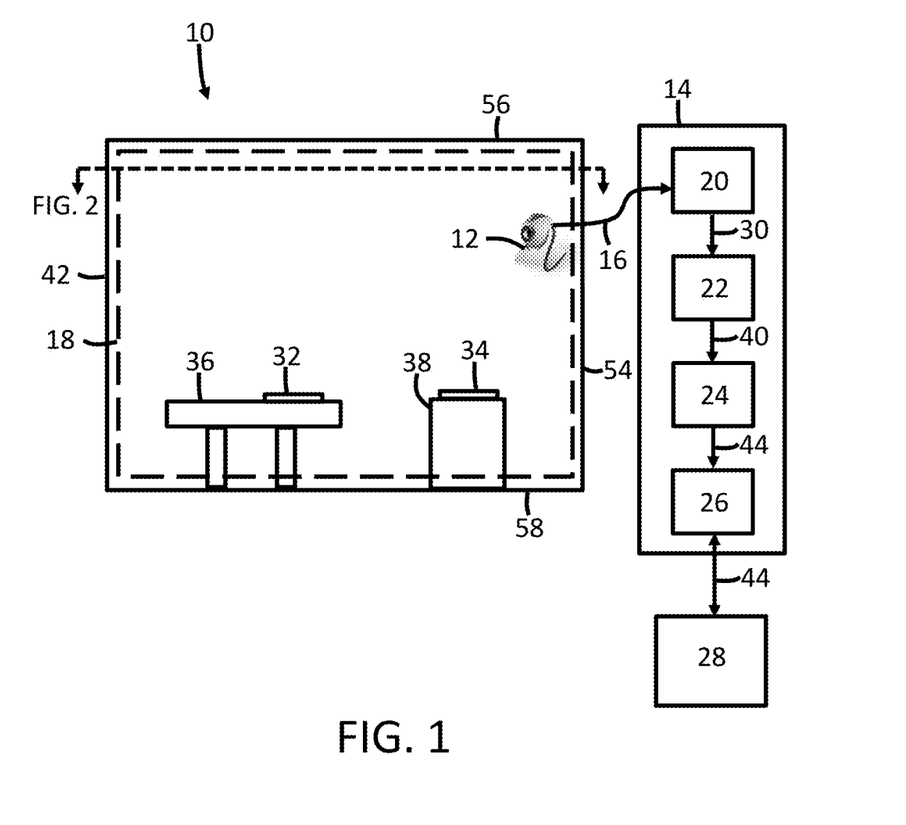
FIG. 1 is a schematic elevation view of the present system having a first camera that images an entirety of a room within a medical care facility.
Figure 2:
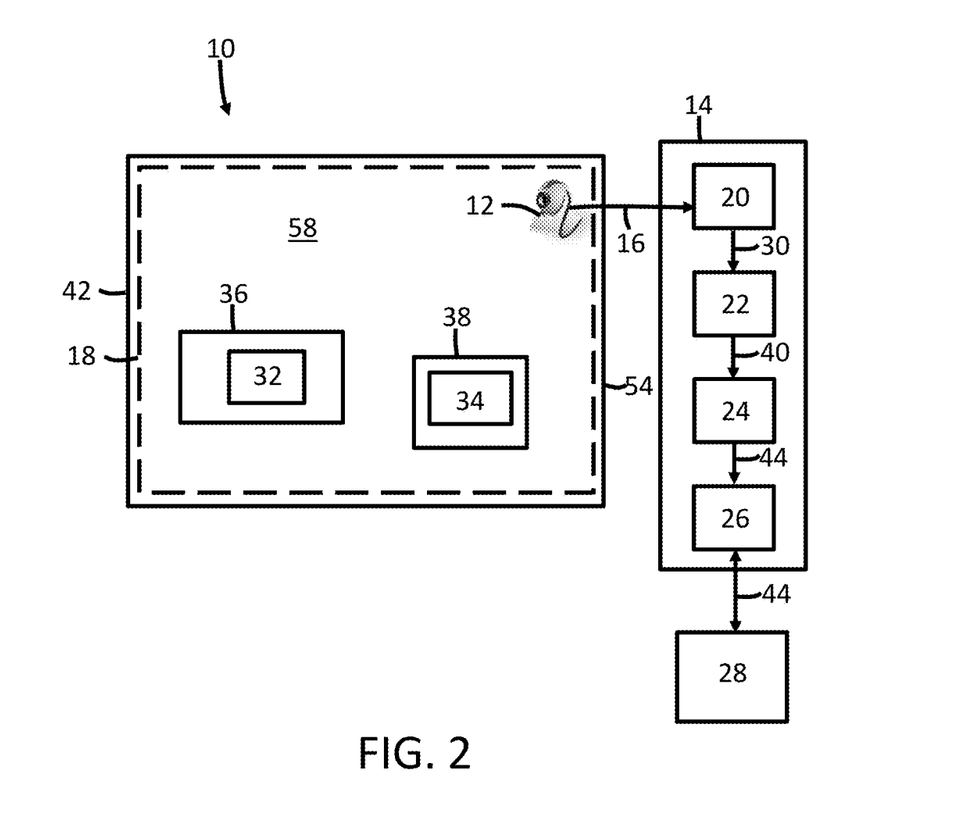
FIG. 2 is a schematic plan view of the system of FIG. 1.

Referring to FIGS. 1 and 2, the system 10 includes at least one first camera 12 and at least one operational metrics device 14.

The first camera 12 generates a first plurality of digital images 16 of a first detection area 18 within a medical care facility over the course of a first detection period (e.g., one day, one week, one month, one year, etc.). Each of the first plurality of digital images 16 is representative of the first detection area 18 at one of a first plurality of discrete imaging times during the first detection period. In some embodiments, each of the first plurality of digital images 16 includes a digital time stamp indicative of the discrete imaging time at which the digital image 16 was captured.

The operational metrics device 14 includes at least an optical code detector 20, a medical object detector 22, and an operational metrics generator 24. In the illustrated embodiments, the operational metrics device 14 additionally includes a database 26, and the system 10 additionally includes a user portal 28.

The optical code detector 20 receives the first plurality of digital images 16 from the first camera 12, and analyzes the first plurality of digital images 16 to generate optical code detection data 30 indicative of the presence or absence of one or more optical codes 32, 34 (e.g., bar codes, QR codes, etc.) within each of the first plurality of digital images 16. Each of the optical codes 32, 34 is disposed on a respective medical object 36, 38 (e.g., a piece of medical equipment), and provides a machine-readable representation of data regarding the respective medical object 36, 38. In some embodiments, the optical code detection data 30 is further indicative of respective locations of the one or more optical codes 32, 34 within each of the first plurality of digital images 16. In such embodiments, the optical code detector 20 can overlay a coordinate map on each of the first plurality of digital images 16, and the optical code detection data 30 can indicate the respective locations of optical codes 32, 34 (e.g., bar codes) relative to the coordinate map. The field of view of the first camera 12 can be selected to remain constant throughout the first detection period, so as to ensure that the coordinate map is overlaid on each of the first plurality of digital images 16 in a consistent manner. In generating the optical code detection data 30, the optical code detector 20 can compare the first plurality of digital images 16 to data stored in a memory device of the optical code detector 20 and/or the database 26. The stored data can provide information regarding, among other things: (i) the types of optical codes 32, 34 that might be present within the first detection area 18; (ii) characteristics of the first camera 12, (e.g., its type, resolution, field of view, etc.); (iii) the shape and/or size of the first detection area 18; (iv) the appropriate coordinate map to be used.

The medical object detector 22 receives the optical code detection data 30 from the optical code detector 20, and analyzes the optical code detection data 30 to generate medical object detection data 40 indicative of at least the presence or absence of each respective medical object 36, 38 within the first detection area 18 at each of the first plurality of discrete imaging times during the first detection period. In embodiments in which the optical code detection data 30 generated by the optical code detector 20 indicates the respective locations of optical codes 32, 34 within each of the first plurality of digital images 16, the medical object detection data 40 generated by the medical object detector 22 can be further indicative of the respective locations of medical objects 36, 38 present within the first detection area 18 at each of the first plurality of discrete imaging times. The respective locations of medical objects 36, 38 can be defined relative to a predetermined point of reference, such as the location of the first camera 12 within the room 42 in which it is positioned. In generating the medical object detection data 40, the medical object detector 22 can compare the optical code detection data 30 to data stored in a memory device of the medical object detector 22 and/or the database 26. The stored data can provide information regarding, among other things: (i) the types of medical objects 36, 38 that might be present within the first detection area 18; (ii) the optical code 32, 34 associated with each medical object 36, 38; and/or (iii) the appropriate point of reference to be used.

The operational metrics generator 24 receives the medical object detection data 40 from the medical object detector 22, and analyzes the medical object detection data 40 to determine, for each respective medical object 36, 38, at least an amount of time that the respective medical object 36, 38 was present within the first detection area 18 during the first detection period. The operational metrics generator 24 generates the operational metrics data 44 based at least partially on the determined amount of time that each respective medical object 36, 38 was present within the first detection area 18 during the first detection period. In some embodiments, the operational metrics generator 24 further determines, and generates the operational metrics data 44 at least partially on the basis of, a number of times that each respective medical object 36, 38 entered and/or exited the first detection area 18 during the first detection period. In embodiments in which the medical object detection data 40 is indicative of the respective locations of medical objects 36, 38 present within the first detection area 18, the operational metrics generator 24 can determine, and can generate the operational metrics data 44 at least partially on the basis of, whether each respective medical object 36, 38 was moved during the first detection period, the number of such movements, and/or the types of such movements.

The operational metrics data 44 provides, and/or can be used to obtain, information that personnel of a medical care facility (e.g., doctors, nurses, medical assistants, administrators, executives, etc.) can use in assessing the medical care facility's operational efficiencies and costs. Such information can include, among other things: (i) the types of medical procedures (e.g., checkups, surgeries, etc.) that were performed in the first detection area 18 during the first detection period; (ii) the amount of time spent performing a particular medical procedure in the first detection area 18; (iii) identities of the medical personnel (e.g., doctors, nurses, medical assistants, etc.) that were involved in a particular medical procedure; (iv) the amount of time a patient spent before, during, and/or after a particular medical procedure; (v) the types of medical objects 36, 38 that were used or were present during a particular medical procedure; (vi) a number of times that a particular medical procedure was started at or before a scheduled start time; (vii) an amount of turnover time that was required between particular medical procedures; (viii) an average number of times that a particular medical procedure was performed during the first detection period; (ix) a number of times that a medical procedure was performed during the first detection period; (x) a cost or average cost of a particular medical procedure; (xii) a number of times medical complications occurred requiring use of a particular medical object 36, 38 or a person associated with the medical object 36, 38; (xiii) a number of times a person associated with a particular medical object 36, 38 entered and/or exited the first detection area 18; (xiv) a number of times a medical infection occurred requiring use of a particular medical object 36, 38 or involvement of a person associated with the medical object 36, 38; (xv) an amount of monetary reimbursement for a medical procedure requiring use of a particular medical object 36, 38 or involvement of a person associated with the medical object 36, 38; (xvi) an amount of profit margin for a medical procedure requiring use of a particular medical object 36, 38 or involvement of a person associated with the particular medical object 36, 38; and/or (xvii) a comparison of a speed at which a medical professional completed a type of medical procedure, and a speed at which a peer medical professional completed the same type of medical procedure.

In generating the operational metrics data 44, the operational metrics generator 24 can compare the medical object detection data 40 to data stored in a memory device of the operational metrics generator 24 and/or the database 26. The stored data can provide a wide variety of information necessary to generate at least some of the above-described information regarding the medical care facility's operational efficiencies and costs.

In embodiments in which the operational metrics device 14 includes a database 26 and the system 10 includes a user portal 28, the database 26 can receive and store the operational metrics data 44, and the user portal 28 can be configured to permit a user to access, manipulate, and/or retrieve (e.g., download) the operational metrics data 44 stored on the database 26. In FIGS. 1 and 2, for example, the user portal 28 is shown to be remotely located relative to the room 42 in which the first camera 12 is located. In other embodiments, the user portal 28 can be positioned in the room 42 in which the first camera 12 is positioned. In such embodiments, the user portal 28 can be used provide the user (e.g., a medical professional) with operational metrics data 44 in real time or near real time. For example, the user portal 28 could be used to provide a medical professional with an alert when an allotted amount of time for a particular medical procedure has been exceeded.

Figure 3:
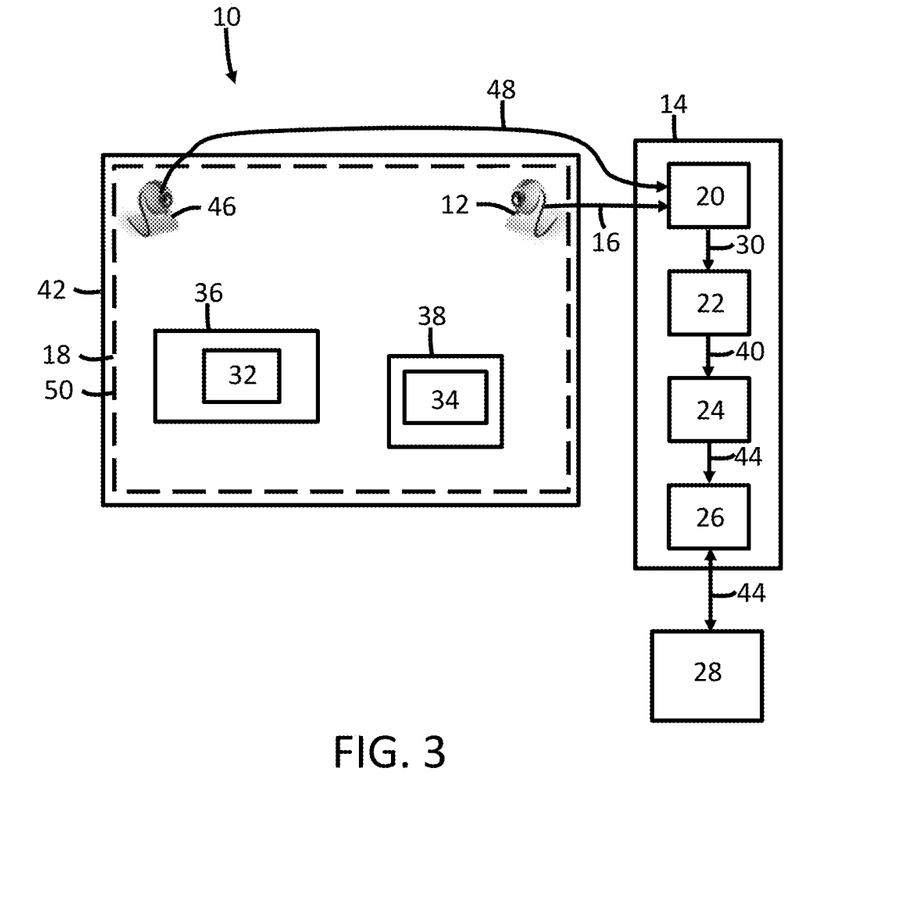
FIG. 3 is a schematic plan view of the present system having first and second cameras that each image an entirety of a room within a medical care facility.
Figure 4:
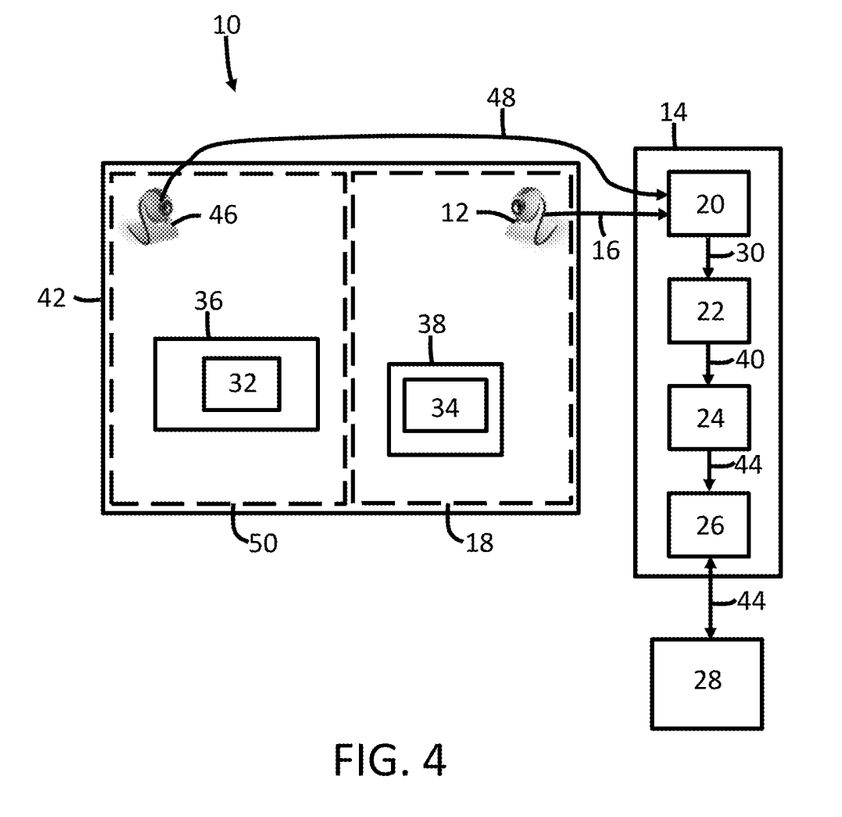
FIG. 4 is a schematic plan view of the present system having first and second cameras that image different portions of a room within a medical care facility.
Figure 5:
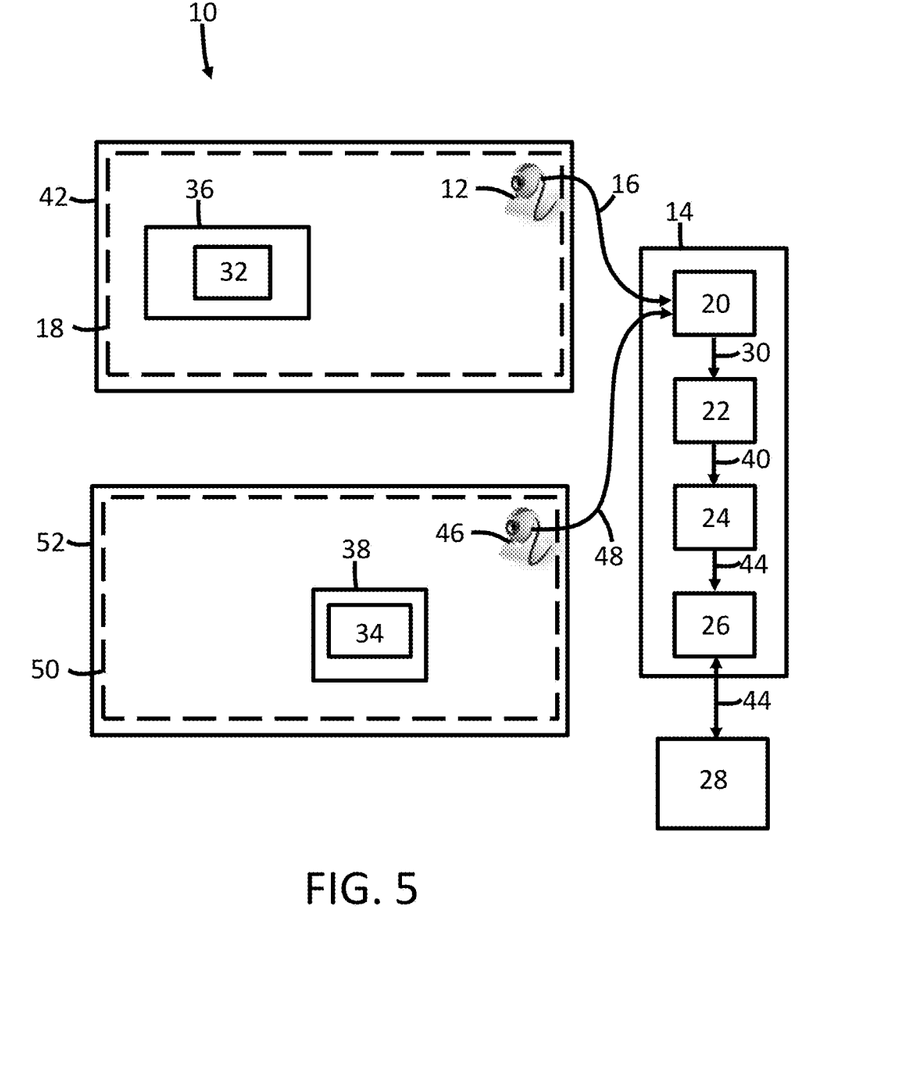
FIG. 5 is a schematic plan view of the present system having a first camera that images an entirety of a first room within a first medical care facility, and a second camera that images an entirety of a second room within a second medical care facility remotely located relative to the first medical care facility.

Referring to FIGS. 3-5, in some embodiments, the system 10 includes at least one first camera 12 and at least one second camera 46. In such embodiments, the first camera 12 generates a first plurality of digital images 16 of a first detection area 18 during a first detection period, and the second camera 46 generates a second plurality of digital images 48 of a second detection area 50 during a second detection period. In some embodiments, the first detection area 18 is at least substantially the same as the second detection area 50. In FIG. 3, for example, the first detection area 18 and the second detection area 50 each cover an entirety of a room 42 (e.g., an operating room) within a medical care facility. That is, the first detection area 18 and the second detection area 50 each correspond to an area defined by the walls of the room 42. In other embodiments, the first detection area 18 and the second detection area 50 only partially overlap one another, or do not overlap one another at all. In FIG. 4, for example, the first detection area 18 covers a first portion of a room 42, the second detection area 50 covers the remaining portion of the same room 42, with no overlap between the first detection area 18 and the second detection area 50. In some embodiments, the first detection area 18 and the second detection area 50 are in separate rooms (i.e., rooms that are remotely located relative to one another). The separate rooms can be in the same medical care facility, or they can be in different medical care facilities remotely located relative to one another. In FIG. 5, for example, the first detection area 18 covers an entirety of a first room 42 within a first medical care facility, and the second detection area 50 covers an entirety of a second room 52 within a second medical care facility remotely located relative to the first medical care facility.

In embodiments in which the system 10 includes a first camera 12 and at least one second camera 46, each of the first plurality of digital images 16 is representative of the first detection area 18 at one of a first plurality of discrete imaging times during a first detection period, and each of the second plurality of digital images 48 is representative of the second detection area 50 at one of a second plurality of discrete imaging times during a second detection period. The second detection period may or may not correspond to (i.e., may or may not be the same as) the first detection period. The operational metrics generator 24 processes the first plurality of digital images 16 and the second plurality of digital images 48, and generates operational metrics data 44 based thereon, in a similar manner to that described above. For example, the optical code detector 20 analyzes the digital images 16, 48 to generate optical code detection data 30 indicative of at least the presence or absence of one or more optical codes 32, 34 within each of the digital images 16, 48. The medical object detector 22 analyzes the optical code detection data 30 and generates medical object detection data 40 indicative of at least the presence or absence of respective medical objects 36, 38 within each of the detection areas 18, 50 during the respective detection periods. The operational metrics generator 24 generates operational metrics data 44 based at least partially on determined amounts of time that the respective medical objects 36, 38 were present within the detection areas 18, 50

Referring to FIGS. 1-5, the one or more cameras 12, 46 each include one or more light sensors that capture and detect light from a respective detection area 18, 50, and generate digital images 16, 48 representative thereof. The light sensors can be one or more of an RGB sensor, a monochromatic (mono) sensor, a near infrared (NIR) sensor, a shortwave infrared (SWIR) sensor, an infrared (IR) sensor, and a hyperspectral sensor. In some embodiments, the one or more cameras 12, 46 each include at least two types of sensors (e.g., an RGB or mono sensor together with a mono, NIR, SWIR, IR, or hyperspectral sensor) that individually and/or collectively generate one or more digital images at each of the plurality of discrete imaging times.

The one or more cameras 12, 46 each have a field of view that is large enough in magnitude that light can be captured and detected from an entirety of a respective detection area 18, 50. The one or more cameras 12, 46 each are configured such that the digital images 16, 48 generated thereby each have a maximum resolution that is high enough in magnitude that the optical code detector 20 is able to accurately detect the presence or absence of one or more optical codes 32, 34 within the digital images 16, 48, and high enough in magnitude that the optical code detector 20 is able to accurately interpret (e.g., de-code) one or more optical codes 32, 34 present within the digital images 16, 48.

There are various commercially-available cameras that are suitable for use with the present system 10, including AXIS P33 Series cameras manufactured by Axis Communications of Lund, Sweden, and various dual sensor cameras manufactured by Qtechnology A/S of Copenhagen, Denmark.

The number of cameras 12, 46 included in the system 10 can vary depending on the number of detection areas 18, 50 and/or rooms 42, 52 that require monitoring. The illustrated embodiments each include only one or two cameras 12, 46; however, in other embodiments, the system 10 can include many more cameras 12, 46. For example, a hospital or network of hospitals could have dozens or hundreds of rooms 42, 52 in which medical procedures are commonly performed, and each of those rooms 42, 52 could have one or more cameras 12, 46 installed therein.

The one or more cameras 12, 46 can each be positioned in one of various different positions within the room 42, 52 in which it is located, depending on the particular application. In FIGS. 1 and 2, for example, the first camera 12 is mounted to a wall 54 of the room 42, at a position closer to the ceiling 56 than the floor 58. In other embodiments, the one or more cameras 12, 46 could be positioned on a ceiling, at a different height on a wall, on another structure, etc.

The number of discrete imaging times within each detection period, and the period between each of the discrete imaging times (i.e., the "sampling rate"), can vary depending on the particular application. Similarly, the respective lengths of the detection periods can vary depending on the particular application.

The one or more detection areas 18, 50 can have various different shapes and sizes depending on the particular application. For example, as described above, each detection area 18, 50 can cover an entirety of a room 42, 52 of a medical care facility (see FIGS. 1-3 and 5), or only a portion of the room 42, 52 (see FIG. 4). The one or more medical care facilities in which the detection areas 18, 50 are located can be any facilities in which medical procedures (e.g., checkups, surgeries, etc.) are commonly performed. Examples of medical care facilities include hospitals, doctor offices, urgent care centers, and triage tents.

Figure 6:
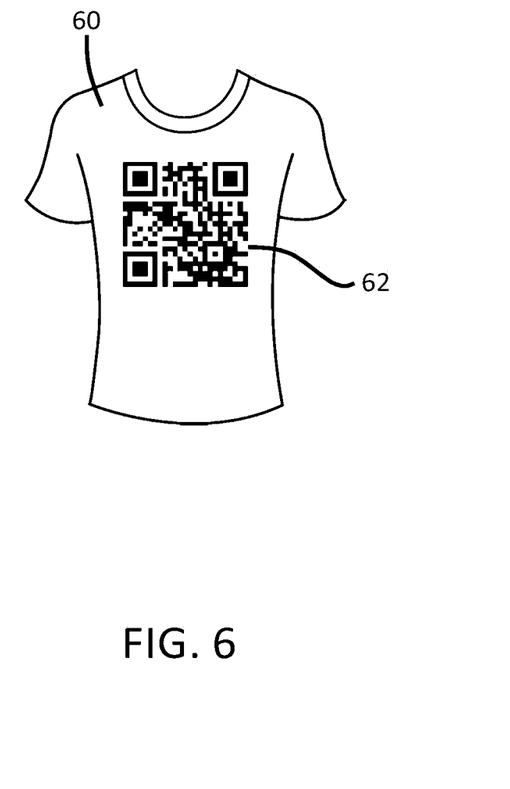
FIG. 6 is a schematic elevation view of a medical object (i.e., a scrub top) having an optical code (i.e., a quick response (QR) code) disposed thereon.

The medical objects 36, 38 on which the optical codes 32, 34 are disposed can be any objects that are commonly present or used during medical procedures. Examples include medical tools, medical equipment, and pieces of medical clothing worn by medical professionals. The medical objects 36, 38 can range in size from portable handheld objects to large, relatively immobile objects. FIGS. 1-5 each illustrate a first medical object 36 in the form of an examination table, and a second medical object 38 in the form of a medical supply cabinet. FIG. 6 illustrates a medical object 60 in the form of a scrub top (i.e., a shirt commonly worn by medical professionals), as will be discussed in more detail below.

The one or more optical codes 32, 34 can be "one-dimensional" bar codes, "matrix" or "two-dimensional" bar codes (e.g., QR codes), or other known types of machine-readable representations of data capable of achieving the functionality described herein. The data represented by each optical code 32, 34 includes information regarding the identity of the respective medical object 36, 38 on which the optical code 32, 34 is disposed. The data can additionally include other information regarding the respective medical object 36, 38, such as information regarding: (i) a structural or functional characteristic of the respective medical object 36, 38; (ii) a manufacturing date of the respective medical object 36, 38; (iii) an expiration date of the respective medical object 36, 38; and/or (iv) a date of first use of the respective medical object 36, 38.

In some embodiments, one or more of the optical codes 32, 34 are made of a known "visible" material (e.g., in the form of a paint, an ink, a sticker, a printed material, etc.) that reflects light at least substantially within a wavelength range that is easily perceived by a naked human eye. In other embodiments, one or more of the optical codes 32, 34 are made of a known "invisible" material (e.g., in the form of a paint, an ink, a sticker, a printed material, etc.) that reflects light at least substantially within a wavelength range (e.g., within the infrared range) that is not easily perceived, or is imperceptible, to a naked human eye.

The respective sizes of the one or more optical codes 32, 34 can vary depending at least partially on the respective resolution capabilities of the one or more cameras 12, 46. That is, the respective sizes of the optical codes 32, 34 are selected to be sufficiently large so as to enable the optical code detector 20 to accurately detect the presence or absence of one or more optical codes 32, 34 within the digital images 16, 48 generated by the one or more cameras 12, 46. In some embodiments, one or more of the optical codes 32, 34 are "normal-sized," meaning they have a size that is at least substantially the same as that of an average barcode. In some embodiments, one or more of the optical codes 32, 34 are "oversized," meaning they have a size that is substantially larger than that of an average barcode. The largest dimension (e.g., a length) of a normal-sized optical code 32, 34 might be approximately 1 inch, 2 inches, 3 inches, or 4 inches, whereas the largest dimension of an oversized optical code 32, 34 might be 6 inches, 7 inches, 8 inches, 9 inches, 10 inches, 11 inches, 12 inches, 13 inches, 14 inches, 15 inches, 16 inches, 17 inches, 18 inches, 19 inches, 20 inches, 21 inches, 22 inches, 23 inches, 24 inches, etc.

The use of oversized optical codes 32, 34 could be unsightly to medical personnel if they are made of a "visible" material. Accordingly, the one or more cameras 12, 46 can be configured to generate digital images 16, 48 having resolutions that are so high in magnitude that the optical code detector 20 is able to accurately detect the presence or absence of normal-sized optical codes 32, 34 within each digital image 16, 48, even when the one or more cameras 12, 46 are positioned at least several feet away from the optical codes 32, 34.

If an optical code 32, 34 is made of an "invisible" material, it is unlikely to be perceived as unsightly, no matter how large the optical code 32, 34 is in size. Thus, aesthetic concerns associated with use of oversized optical codes 32, 34 can be reduced or eliminated by making oversized optical codes 32, 34 with an "invisible" material. To illustrate this point, FIG. 6 depicts a medical object 60 in the form of a scrub top (hereinafter "scrub top 60"). The optical code 62 disposed on the front of the scrub top 60 is in the form of a QR code, and is far larger in size than an average QR code. If the optical code 62 were made of a "visible" material, medical personnel might protest wearing such a scrub top 60 due to its unsightliness. However, medical personnel would be more inclined to wear the scrub top 60 if the optical code 62 disposed thereon were made of an "invisible." In fact, medical personnel wearing the scrub top 60 might not even be aware of the presence of the optical code 62 if it is made of an "invisible" material.

In view of the above, the use of optical codes 32, 34 made of an "invisible" material can be advantageous in that it makes use of oversized optical codes 32, 34 more feasible. The use of oversized optical codes 32, 34 can be advantageous in that it makes use of relatively less expensive cameras 12, 46 (e.g., having lower resolution capabilities) more feasible. The use of optical codes 32, 34 made of "invisible" material can also be advantageous in that such optical codes 32, 34 can be imaged by cameras 12, 46 having appropriate sensors even in a relatively dark environment (e.g., an environment with relatively little white light illumination). There are many medical procedures that are performed in a relatively dark environment.

In some embodiments in which at least substantially all of the one or more optical codes 32, 34 are made of an "invisible" material, none of the one or more cameras 12, 46 include a light sensor (e.g., an RGB or mono sensor) configured to detect light within a wavelength range that is easily perceived by a naked human eye; instead, each of the one or more cameras 12, 46 includes only one or more sensors (e.g., NIR, SWIR, IR, and/or hyperspectral sensors) configured to detect light at least substantially within a wavelength range (e.g., within the infrared range) that is not easily perceived, or is imperceptible, to a naked human eye.

The functionality of the operational metrics device 14, and/or the various components thereof, can be implemented using analog and/or digital hardware (e.g., counters, switches, logic devices, memory devices, programmable processors, non-transitory computer-readable storage mediums), software, firmware, or a combination thereof. The operational metrics device 14, and/or the various component thereof, can be specially constructed to perform the desired functionality, and/or can include one or more general purpose computers selectively configured to perform the desired functionality. In some embodiments, the operational metrics device 14 can perform one or more of the functions described herein by executing software, which can be stored, for example, on a non-transitory computer-readable storage medium. In view of the present disclosure, a person having ordinary skill in the art would be able to adapt (e.g., construct, program) the operational metrics device 14 to perform the functionality described herein without undue experimentation.

Although the components of the operational metrics device 14 are described as being discrete components separate from one another, in some embodiments one or more of the components can be combined into a single component. Similarly, although the operational metrics device 14 is described as being a discrete component separate from the one or more cameras 12, 46, in some embodiments at least one component of the operational metrics device 14 can be included in the one or more cameras 12, 46. Additionally or alternatively, one or more functions of the operational metrics device 14 can be performed by the one or more cameras 12, 46. In some instances, this could be advantageous in that it could "decentralize" data traffic and processing on the operational metrics device 14, and could thereby improve (e.g., speed up) performance of the operational metrics device 14 and/or the system 10 as a whole.

The various connections between the components of the system 10 can include wired and/or wireless connections. Wired connections can be made by any type of conductive transmission line. In some embodiments, one or more components of the system 10 can be connected via a network connection (e.g., via the Internet and/or via a personal area network (PAN), a local area network (LAN), a wide area network (WAN), etc.).

Referring to FIGS. 1 and 2, another aspect of the present invention involves a method that includes the steps of: (i) generating a first plurality of digital images 16 of at least a first detection area 18 within a medical care facility over the course of a first detection period, each of the first plurality of digital images 16 being representative of the first detection area 18 at one of a first plurality of discrete imaging times during the first detection period; (ii) generating optical code detection data 30 indicative of at least a presence or absence of one or more optical codes 32, 34 within each of the first plurality of digital images 16, each of the one or more optical codes 32, 34 being disposed on a respective medical object 36, 38 and providing a machine-readable representation of data regarding the respective medical object 36, 38; (iii) using the optical code detection data 30 to generate medical object detection data 40 indicative of at least a presence or absence of each respective medical object 36, 38 within the first detection area 18 at each of the first plurality of discrete imaging times during the first detection period; (iv) using the medical object detection data 40 to determine at least an amount of time that each respective medical object 36, 38 was present within the first detection area 18 during the first detection period; and (v) generating operational metrics data 44 based at least partially on the determined amount of time that each respective medical object 36, 38 was present within the first detection area 18 during the first detection period.

As will be apparent in view of the above-described functionality of the system 10 and the various components thereof, the steps of the method can include various sub-steps, and/or various other steps in addition to the above-described steps. Although the steps of the method are set forth in a particular order using numeric and/or alphanumeric labels, the labels are used merely for convenient identification of steps, and are not intended to imply, specify, or require a particular order of carrying out such steps. Furthermore, in some embodiments, the method can include more or less steps than those discussed herein.

The terms "analyzing," "determining," "generating," "comparing," and variations thereof, are each used herein to refer to one or more actions and/or processes that can be implemented, for example, via a programmable processor or similar electronic computing device by manipulating and/or transforming data within the processor's memory into other data within the processor's memory.

The present disclosure describes aspects of the present invention with reference to the exemplary embodiments illustrated in the drawings; however, aspects of the present invention are not limited to the exemplary embodiments illustrated in the drawings. It will be apparent to those of ordinary skill in the art that aspects of the present invention include many more embodiments. Accordingly, aspects of the present invention are not to be restricted in light of the exemplary embodiments illustrated in the drawings. It will also be apparent to those of ordinary skill in the art that variations and modifications can be made without departing from the true scope of the present disclosure. For example, in some instances, one or more features disclosed in connection with one embodiment can be used alone or in combination with one or more features of one or more other embodiments.

What is claimed is:

1. A system for generating operational metrics data for a medical care facility, the system comprising:
   a first camera configured to generate a first plurality of digital images of a first detection area during a first detection period, each of the first plurality of digital images representative of the first detection area at one of a first plurality of discrete imaging times during the first detection period;
   a second camera configured to generate a second plurality of digital images of a second detection area during a second detection period, each of the second plurality of digital images representative of the second detection area at one of a second plurality of discrete imaging times during the second detection period; and
   an operational metrics device configured to receive the first plurality of digital images and the second plurality of digital images via one or more wired and/or wireless connections, the operational metrics device having:
      an optical code detector configured to generate optical code detection data indicative of at least a presence or absence of one or more optical codes within each of the first plurality of digital images, and a presence or absence of the one or more optical codes within each of the second plurality of digital images, each of the one or more optical codes disposed on a respective medical object and having a largest dimension of at least 3 inches;
      a medical object detector including a non-transitory computer-readable storage medium storing a software configured to receive the optical code detection data via one or more wired and/or wireless connections and generate medical object detection data therefrom, the medical object detection data indicative of at least a presence or absence of each respective medical object within the first detection area at each of the first plurality of discrete imaging times during the first detection period, and a presence or absence of each respective medical object within the second detection area at each of the second plurality of discrete imaging times; and
      an operational metrics generator configured to receive the medical object detection data from the medical object detector via one or more wired and/or wireless connections, and analyze the medical object detection data to determine, for each respective medical object, at least an amount of time that each respective medical object was present within the first detection area during the first detection period, and an amount of time that each respective medical object was present within the second detection area during the second detection period;
   wherein the operational metrics generator is configured to generate operational metrics data based at least partially on the determined amount of time that each respective medical object was present within the first detection area during the first detection period, and the determined amount of time that each respective medical object was present within the second detection area during the second detection period.

2. The system of claim 1, wherein each of the one or more optical codes provides a machine-readable representation of data regarding the respective medical object on which the optical code is disposed.

3. The system of claim 1, wherein the first detection area is the same as the second detection area.

4. The system of claim 1, wherein the first detection area and the second detection area only partially overlap one another.

5. The system of claim 1, wherein the first detection area and the second detection area do not overlap one another at all.

6. The system of claim 1, wherein the first detection area and the second detection area are in a same room of a medical care facility.

7. The system of claim 1, wherein the first detection area is in a first room, and the second detection area is in a second room remotely located relative to the first room.

8. The system of claim 7, wherein the first room is in a first medical care facility, and the second room is in a second medical care facility remotely located relative to the first medical care facility.

9. The system of claim 1, wherein the first detection area covers an entirety of a room within a medical care facility.

10. The system of claim 1, wherein the respective medical object is a piece of medical clothing configured to be worn by a medical professional.

11. The system of claim 1, wherein each of the one or more optical codes is a one-dimensional bar code.

12. The system of claim 1, wherein each of the one or more optical codes is a two-dimensional bar code.

13. The system of claim 12, wherein each of the one or more optical codes is a QR code.

14. The system of claim 1, wherein at least one of the one or more optical codes reflects light within a wavelength range that is perceptible to a naked human eye.

15. The system of claim 1, wherein at least one of the one or more optical codes reflects light within a wavelength range that is imperceptible to a naked human eye.

16. The system of claim 1, wherein the first camera includes a first sensor configured to capture and detect light from the first detection area, and a second sensor configured to capture and detect light from the first detection area; and
   wherein the first sensor is an RGB sensor or a monochromatic sensor, and the second sensor is at least one of a monochromatic sensor, a near infrared sensor, a short-wave infrared sensor an infrared sensor, and a hyperspectral sensor.

17. The system of claim 1, wherein all of the one or more optical codes reflect light within a wavelength range that is imperceptible to a naked human eye;
   wherein the first camera includes a light sensor configured to detect light within a wavelength range that is imperceptible to a naked human eye; and
   wherein the system does not include any light sensor configured to detect light within a wavelength range that is perceptible to a naked human eye.

18. The system of claim 1, wherein the optical code detection data is further indicative of respective locations of the one or more optical codes within each of the first plurality of digital images;
   wherein the medical object detection data is further indicative of respective locations of each respective medical object present within the first detection area at each of the first plurality of discrete imaging times; and wherein the operational metrics generator is further configured to determine, and generate the operational metrics data at least partially based on, whether each respective medical object was moved during the first detection period.

19. The system of claim 1, wherein the operational metrics generator is further configured to determine, and generate the operational metrics data at least partially based on, a number of times that each respective medical object entered and/or exited the first detection area during the first detection period.

20. The system of claim 1, further comprising a user portal configured to permit a user to access, manipulate, and/or retrieve the operational metrics data generated by the operational metrics generator.

21. The system of claim 20, wherein the first camera is positioned in a room of a medical care facility, and the user portal is remotely located relative to the room.

22. The system of claim 1, wherein the first camera and the operational metrics device are discrete components that are remotely located relative to one another.

23. The system of claim 22, wherein the first camera is positioned in a room of a medical care facility, and the operational metrics device is remotely located relative to the room.

24. The system of claim 1, wherein at least one of the optical code detector, the medical object detector, and the operational metrics generator is included within the first camera.

25. The system of claim 1, wherein at least one of the optical code detector, the medical object detector, and the operational metrics generator is remotely located relative to the first camera.

26. The system of claim 1, wherein one or more components are connected via a network connection, the network connection being at least one of an Internet connection, a personal area network connection, a local area network connection, and a wide area network connection.

27. The system of claim 1, wherein each of the one or more optical codes is a QR code.

28. The system of claim 1, wherein each of the one or more optical codes has a largest dimension of at least 6 inches.

29. A method for generating operational metrics data for a medical care facility, the method comprising:
generating a first plurality of digital images of at least a first detection area within a medical care facility during a first detection period, each of the first plurality of digital images representative of the first detection area at one of a first plurality of discrete imaging times during the first detection period;
generating a second plurality of digital images of at least a second detection area within a medical care facility during a second detection period, each of the second plurality of digital images representative of the first detection area at one of a second plurality of discrete imaging times during the second detection period;
providing an optical code detector to receive the first plurality of digital images and the second plurality of digital images via one or more wired and/or wireless connections;
using the optical code detector to generate optical code detection data indicative of at least a presence or absence of one or more optical codes within each of the first plurality of digital images, and a presence or absence of the one or more optical codes within each of the second plurality of digital images, each of the one or more optical codes disposed on a respective medical object and having a largest dimension of at least 3 inches;
providing a medical object detector including a non-transitory computer-readable storage medium on which a software is stored, and executing the software to receive the optical code detection data via one or more wired and/or wireless connections and use the optical code detection data to generate medical object detection data indicative of at least a presence or absence of each respective medical object within the first detection area at each of the first plurality of discrete imaging times during the first detection period;
using an operation metrics generator to receive the medical object detection data via one or more wired and/or wireless connections and use the medical object detection data to determine at least an amount of time that each respective medical object was present within the first detection area during the first detection period, and an amount of time that each respective medical object was present within the second detection area during the second detection period; and
using an operational metrics generator to generate operational metrics data based at least partially on the determined amount of time that each respective medical object was present within the first detection area during the first detection period, and the determined amount of time that each respective medical object was present within the second detection area during the second detection period.

30. The system of claim 29, wherein each of the one or more optical codes is a QR code.

31. The method of claim 29, wherein each of the one or more optical codes has a largest dimension of at least 6 inches.

* * * * *